United States Patent [19]

Poser

[11] Patent Number: 4,683,242
[45] Date of Patent: Jul. 28, 1987

[54] TRANSDERMAL TREATMENT FOR PAIN AND INFLAMMATION WITH 2-AMINO-3-AROYLBENZENEACETIC ACIDS, SALTS AND ESTERS

[75] Inventor: Richard G. Poser, Richmond, Va.

[73] Assignee: A. H. Robins Company, Incorporated, Richmond, Va.

[21] Appl. No.: 792,269

[22] Filed: Oct. 28, 1985

[51] Int. Cl.$^4$ .................. A61K 31/24; A61K 31/195
[52] U.S. Cl. ............................ 514/539; 514/562
[58] Field of Search ........................ 514/562, 539

[56] References Cited

U.S. PATENT DOCUMENTS 4,045,576  8/1977  Welstead et al. ............... 260/517
4,503,073  5/1985  Walsh et al. ................... 514/539

Primary Examiner—Stanley J. Friedman

[57] ABSTRACT

A method is disclosed for treating pain and/or inflammation by transdermal administration of 2-amino-3-benzoylbenzeneacetic acids, salts and esters having the formula

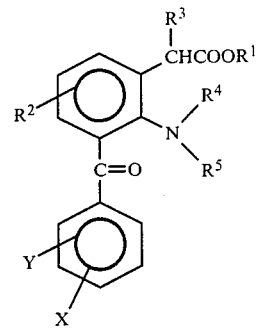

wherein $R^1$ is hydrogen, loweralkyl or a pharmaceutically acceptable cation; $R^2$ is hydrogen, halogen, loweralkyl or loweralkoxy; $R^3$, $R^4$ and $R^5$ are hydrogen or loweralkyl; X is hydrogen, halogen, loweralkyl, hydroxy, loweralkoxy, nitro, trifluoromethyl or loweralkylthio; Y is hydrogen, loweralkyl, loweralkoxy, nitro or trifluoromethyl and hydrates and alcoholates thereof.

80 Claims, No Drawings

TRANSDERMAL TREATMENT FOR PAIN AND INFLAMMATION WITH 2-AMINO-3-AROYLBENZENEACETIC ACIDS, SALTS AND ESTERS

BACKGROUND OF THE INVENTION

1. Field of Invention

The present invention relates to the use of certain 2-amino-3-benzoylbenzeneacetic acid, salts and esters thereof in transdermal administration to animals and humans to control pain and/or inflammation.

2. Information Disclosure Statement

Certain 2-amino-3-benzoylbenzenacetic acids are disclosed in U.S. Pat. Nos. 4,045,576, 4,503,073, Great Britain Pat. No. 2,093,027, J. MED. CHEM., Vol. 25, pp 446–451 (1982) and Vol. 27, pp 1379–1388 (1984), all of which disclosures and methods of preparation disclosed therein are herein incorporated by reference. Oral, parenteral and intravenous administration of the compounds to control inflammaton and alleviate pain have been disclosed in the foregoing references. None of the above references disclose the transdermal method of administration of this invention.

Japan Kokai No. 201710/1983 published Nov. 24, 1983 discloses oral mucosal administration of Amfenac ® sodium or calcium salt in a stabilized pharmaceutical paste for the treatment of inflammation of the oral cavity. Amphenac ® is 2-amino-3-benzoylbenzeneacetic acid, one of the compounds useful in the present invention.

Famaey, J. B., in J. BELGE, RHUMATOL. MED. PHYS. (Belgium) Vol. 30, pp 129–141 (1975) discloses the need for studying sonophoresis in connection with creams prepared from non-steroidal anti-inflammatory drugs including Ketoprofen ®, among others. Ketoprofen ® is 3-benzoyl-α-methylbenzeneacetic acid. The compounds of the present invention differ from Ketoprofen ® in structure in that an amino group is always present in the 2-position of the primary ring.

U.S. Pat. No. 4,404,198 discloses a combination of phenylacetic acid and eugenol as a topical application to inflamed skin of animals and humans.

Remington's Pharmaceutical Sciences, 16th Ed. (1985), page 1523 states:

"Electrolytes in solution penetrate the skin poorly. Ionization of a weak electrolyte substantially reduces its permeability, e.g., sodium salicylate permeates poorly compared with salicylic acid."

In constrast to this, the salts of the 2-amino-3-benzoylbenzeneacetic acids encompassed by Formula I hereinbelow are highly potent as anti-inflammatory and analgesic agents when administered transdermally.

SUMMARY AND OBJECTS OF THE INVENTION

The invention is more specifically concerned with transdermal administration of 2-amino-3-benzoylbenzeneacetic acids, esters and salts having the formula:

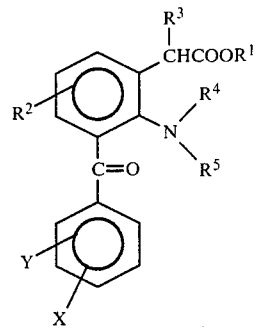

Formula I wherein;
$R^1$ is hydrogen, loweralkyl or a pharmaceutically acceptable cation forming a pharmaceutically acceptable salt;
$R^2$ is hydrogen, halogen, loweralkyl or loweralkoxy;
$R^3$, $R^4$ and $R^5$ are hydrogen or loweralkyl;
X is hydrogen, halogen, loweralkyl, hydroxy, loweralkoxy, nitro, trifluoromethyl or loweralkylthio;
Y is hydrogen, loweralkyl, loweralkoxy, nitro or trifluoromethyl and the hydrates thereof. The pharmaceutically acceptable salts are an alternative term to $R^1$ being a pharmaceutically acceptable cation which includes hydrates and alcoholates thereof and of any of the acids should they occur.

In the further definition of symbols in the formulas hereof and where they occur elsewhere throughout this specification, the terms have the following significance.

The term "loweralkyl" as used herein includes straight and branched chain radicals up to six carbons inclusive, preferably no more than four carbons, and is exemplified by such groups as methyl, ethyl, propyl, isopropyl, butyl, sec. butyl, tertiary butyl, amyl, isoamyl and hexyl. The term "loweralkoxy" has the formula O-loweralkyl.

The term "halogen" when referred to herein includes chlorine, bromine, fluorine and iodine.

When used herein the term "benzoyl" refers to the unsubstituted benzoyl radical, the monosubstituted benzoyl radical and the disubstituted benzoyl radical.

The present invention is based on the discovery that pharmacologically effective doses of compounds of Formula I could be transported through animal skin. Compared to oral administration transdermal administration avoids exposure to stomach acids and possible degradation.

It is therefore an object of the present invention to provide effective relief of pain and inflammation by transdermal administration of 2-amino-3-benzoylbenzeneacetic acids, salts and esters thereof to humans and animals.

Another object is to avoid or ameliorate gastric irritation by transdermal administration of 2-amino-3-benzoylbenzeneacetic acids, salts, and esters thereof, as opposed to oral administration.

Another object is to provide aqueous pharmaceutical compositions which are stable against decomposition of the 2-amino-3-benzoylbenzeneacetic acids, salts, and esters.

Still another object is to provide relief of pain and inflammation due to arthritic conditions by transdermal administration of 2-amino-3-benzoylbenzeneacetic acids, salts and esters to animals and humans.

Additional objects will become obvious to one skilled in the art and will become apparent hereinafter.

DETAILED DESCRIPTION OF THE INVENTION

The present invention encompasses the methods of use of the compounds of Formula I in transdermal administration to animals and humans for the treatment of pain and inflammation and pharmaceutical compositions therefor suitable for external application to a live animal body.

In the method of this invention, the compounds of Formula I are applied externally to the skin of animals and humans in the form of creams, lotions, ointments, solutions, suspensions and occlusive devices. The rate of delivery may be modified or controlled by semipermeable membranes, composition of matrix and by chemical enhancers. The carriers, occlusive devices and methods of administration are discussed more in detail hereinbelow.

Compared to oral and intravenous administrations, transdermal delivery of these agents prolongs duration of therapeutic activity and causes less gastric irritation than is found in oral administration.

When the pharmaceutical compositions are in liquid form such as a cream or when the reservoir of an occlusive device contains the compound as a liquid pharmaceutical composition, the preferred composition has an oil-in-water-base carrier (i.e., over 50% water) and a pH of about 6.5 to 8.0. Obviously, one or more compounds of Formula I may be employed.

Examples 1–76 given below of Formula I illustrate compounds useful in the present invention but are not limiting. Compounds of Examples 1–59 were prepared as disclosed in the above references and are given below by name. Compounds of Examples 60–76 do not appear in the above references and preparation is given herein in detail. The structures of the compounds are in Table I. Examples 77–86 illustrate how some of the preferred compounds may be formulated and applied transdermally but they are not limiting.

| Example No. | Name |
|---|---|
| 1 | 2-Amino-3-benzoylbenzeneacetic acid. |
| 2 | 2-Amino-3-benzoyl-5-chlorobenzeneacetic acid, hemihydrate. |
| 3 | 2-Amino-3-benzoyl-5-methoxybenzeneacetic acid, sodium salt, sesquihydrate. |
| 4 | 2-Amino-3-benzoylbenzeneacetic acid, sodium salt, dihydrate. |
| 5 | 2-Amino-3-benzoylbenzeneacetic acid, ethyl ester. |
| 6 | 2-Amino-3-(4-chlorobenzoyl)benzeneacetic acid, sodium salt, monohydrate. |
| 7 | 2-Amino-3-benzoylbenzeneacetic acid, potassium salt, monohydrate. |
| 8 | 2-Amino-3-(4-chlorobenzoyl)benzeneacetic acid, ethyl ester. |
| 9 | 2-Amino-3-(4-fluorobenzoyl)benzeneacetic acid. |
| 10 | 2-Amino-3-(4-fluorobenzoyl)benzeneacetic acid, sodium salt, monohydrate. |
| 11 | 2-Amino-3-(4-methoxybenzoyl)benzeneacetic acid. |
| 12 | 2-Amino-3-benzoylbenzeneacetic acid, magnesium salt, trihydrate. |
| 13 | 2-Amino-3-benzoylbenzeneacetic acid, calcium salt, dihydrate. |
| 14 | 2-Amino-3-benzoylbenzeneacetic acid, sodium salt, monohydrate. |
| 15 | 2-Amino-3-(4-fluorobenzoyl)-5-methylbenzeneacetic acid, sodium salt, monohydrate. |
| 16 | 2-Amino-3-(4-chlorobenzoyl)-5-methylbenzeneacetic acid, sodium salt. |
| 17 | 2-Amino-3-[(4-methylthio)benzoyl]benzeneacetic acid, sodium salt, monohydrate. |
| 18 | 2-Amino-3-[(4-methylthio)benzoyl]-5-chlorobenzeneacetic acid, sodium salt, hydrate [4:3]. |
| 19 | 2-Amino-3-[(4-methylthio)benzoyl]-5-fluorobenzeneacetic acid, sodium salt. |
| 20 | 2-Amino-3-benzoyl-4-methylbenzeneacetic acid, sodium salt, hydrate [4:1]. |
| 21 | 2-Amino-3-(4-bromobenzoyl)benzeneacetic acid, sodium salt. |
| 22 | 2-Amino-3-benzoyl-6-methylbenzeneacetic acid, sodium salt, hydrate [4:1]. |
| 23 | 2-Amino-3-benzoyl-5-methylbenzeneacetic acid, sodium salt, hemihydrate. |
| 24 | 2-Amino-3-(2,4-dichlorobenzoyl)benzeneacetic acid, sodium salt, hemihydrate. |
| 25 | 2-Amino-3-[4-(methylthio)benzoyl]-5-methylbenzeneacetic acid, sodium salt dihydrate. |
| 26 | 2-Amino-3-(4-methylbenzoyl)-5-methylbenzeneacetic acid. |
| 27 | 2-Amino-3-(4-chlorobenzoyl)-5-fluorobenzeneacetic acid, sodium salt, hydrate [4:1]. |
| 28 | 2-Amino-3-(2,4-dichlorobenzoyl)-5-methylbenzeneacetic acid, sodium salt, hemihydrate. |
| 29 | 2-Amino-3-(4-bromobenzoyl)-5-chlorobenzeneacetic acid, sodium salt. |
| 30 | 2-Amino-3-(4-chlorobenzoyl)-5-methoxybenzeneacetic acid, sodium salt, hydrate [4:1]. |
| 31 | 2-Amino-3-(4-bromo-2-chlorobenzoyl)benzeneacetic acid, sodium salt, hemihydrate. |
| 32 | 2-Amino-3-(4-bromo-2-chlorobenzoyl)-5-chlorobenzeneacetic acid, sodium salt, monohydrate. |
| 33 | 2-Amino-3-(4-bromobenzoyl)-5-methylbenzeneacetic acid, sodium salt. |
| 34 | 2-Amino-3-(4-iodobenzoyl)-5-chlorobenzeneacetic acid, sodium salt, hemihydrate. |
| 35 | 2-Amino-3-(4-bromobenzoyl)-5-fluorobenzeneacetic acid, sodium salt, monohydrate. |
| 36 | 2-Amino-3-(4-bromobenzoyl)-5-bromobenzeneacetic acid, sodium salt, hemihydrate. |
| 37 | 2-Amino-3-(4-bromobenzoyl)-5-methoxybenzeneacetic acid, sodium salt. |
| 38 | 2-Amino-3-(3,4-dichlorobenzoyl)benzeneacetic acid, sodium salt, hydrate [4:7]. |
| 39 | 2-Amino-3-(4-fluorobenzoyl)benzeneacetic acid, sodium salt. |
| 40 | 2-Amino-3-(4-methoxybenzoyl)benzeneacetic acid, sodium salt, hemihydrate. |
| 41 | 2-Amino-3-benzoyl-5-chlorobenzeneacetic acid, sodium salt. |
| 42 | 2-Amino-3-(2-chlorobenzoyl)benzeneacetic acid, sodium salt, monohydrate. |
| 43 | 2-Amino-3-(3-chlorobenzoyl)benzeneacetic acid, sodium salt, hemihydrate. |
| 44 | 2-Amino-3-benzoyl-5-fluorobenzeneacetic acid, sodium salt, hemihydrate. |
| 45 | 2-Amino-3-(4-methylbenzoyl)benzeneacetic acid, sodium salt. |
| 46 | 2-Amino-3-[4-(trifluoromethyl)benzoyl]benzeneacetic acid, sodium salt, hemihydrate. |
| 47 | 2-Amino-3-(2-methylbenzoyl)benzeneacetic acid, sodium salt, hydrate [4:1]. |
| 48 | 2-Amino-3-benzoyl-4-chlorobenzeneacetic acid, sodium salt, hydrate [4:1]. |
| 49 | 2-Amino-3-(4-chlorobenzoyl)-5-chlorobenzeneacetic acid, sodium salt. |
| 50 | 2-Amino-3-(4-fluorobenzoyl)-5-fluorobenzeneacetic acid, sodium salt. |
| 51 | 2-Amino-3-(4-methylbenzoyl)-5-fluorobenzeneacetic acid, sodium salt, hydrate [4:1]. |
| 52 | 2-Amino-3-(2,4-dichlorobenzoyl)-5-fluorobenzeneacetic acid, sodium salt, 2-propanol [2:1]. |
| 53 | 2-Amino-3-(2,4-dimethylbenzoyl)benzeneacetic acid, sodium salt. |
| 54 | 2-Amino-3-(4-hydroxybenzoyl)-5-chlorobenzeneacetic acid, hydrate [4:3]. |
| 55 | 2-Amino-3-(4-methylbenzoyl)-5-chlorobenzeneacetic acid, sodium salt, hydrate [4:3]. |
| 56 | 2-Amino-3-(4-chlorobenzoyl)-5-bromobenzeneacetic acid, sodium salt, hemihydrate. |

-continued

| Example No. | Name |
|---|---|
| 57 | 2-Amino-3-(4-iodobenzoyl)benzeneacetic acid, sodium salt, hydrate [4:1]. |
| 58 | 2-Dimethylamino-3-benzoylbenzeneacetic acid. |
| 59 | 2-Amino-3-benzoyl-α-methylbenzeneacetic acid, sodium salt, dihydrate. |

EXAMPLE 60

2-Amino-3-(benzoylbenzeneacetic acid, zinc salt, hemihydrate

To a solution of 14.7 g (0.05 mole) of 2-amino-3-benzoylbenzeneacetic acid, sodium salt monohydrate in 125 ml of water was added a solution of 7.2 g (0.025 mole) of zinc sulfate heptahydrate in 25 ml of water. The solid which precipitated was collected by filtration, washed with water and methyl alcohol, and dried to yield 12.5 g (86%) of title compound, a yellow powder, m.p. 144° C. (with decomposition).

Analysis: Calculated for $C_{30}H_{25}N_2O_{6.5}Zn$: C, 61.82; H, 4.32; N, 4.81 Found: C, 61.47; H, 4.14; N, 4.88.

EXAMPLE 61

2-Amino-3-benzoyl-5-chlorobenzeneacetic acid ethyl ester

A solution of 3.12 g (0.1 mole) of 2-amino-3-benzoyl-5-chlorobenzeneacetic acid, sodium salt in 250 ml of dry tetramethylfuran was treated with 44 g of ethyl iodide (0.3 mole) under nitrogen and stirred for 2 hours. The resulting solution was then added to 1 liter of water and extracted several times with ethyl ether. The combined ether layers were washed with water, dried over sodium sulfate, filtered and stripped to yield a solid yellow residue. This material was recrystallized from absolute ethyl alcohol to give 1.5 g, yellow needles, m.p. 80°–82° C.

Analysis: Calculated for $C_{17}H_{16}ClNO_3$: C, 64.26; H, 5.08; N, 4.41 Found: C, 64.17; H, 5.01; N, 4.39.

EXAMPLE 62

2-Amino-3-(4-chlorobenzoyl)-α-methylbenzeneacetic acid sodium salt, hydrate, 2-propanol [4:1:2]

This compound was prepared by the procedure used to synthesize the compound of Example 51. A combination of 10.7 g (0.038 mole of 7-(4-chlorobenzoyl)-1,3-dihydro-3-methyl-2H-indol-2-one and 180 ml of 3N sodium hydroxide gave, after recrystallization from 2-propanol, 2.7 g (22%) of title compound, bright yellow crystals, m.p. 130°–140° C. (loses solvent).

Analysis: Calculated for $C_{16}H_{13}ClNNaO_3 \cdot 0.5C_3H_8O \cdot 0.25H_2O$: C, 58.34; H, 4.90; N, 3.89 Found C, 58.16; H, 4.96; N, 3.85.

EXAMPLE 63

2-Amino-3-(4-chlorobenzoyl)-5-fluoro-α-methylbenzeneacetic acid, sodium salt

A mixture of 6.6 g (0.022 mole) of 7-(4-chlorobenzyl)-5-fluoro-1,3-dihydro-3-methyl-2H-indol-2-one and 180 ml of 3N sodium hydroxide was heated at 100° C. under a nitrogen atmosphere for 12 hr. The mixture was diluted with about 600 ml of water, titrated to pH=7.5 with concentrated hydrochloric acid and filtered. The filtrate was concentrated under reduced pressure and the crystalline residue was triturated with hot absolute ethyl alcohol. The mixture was filtered and the filtrate was again concentrated at reduced pressure. The residue was recrystallized from absolute ethyl alcohol and the resulting solid was rinsed with diethyl ether to give 2.7 g (38%) of title compound, a yellow powder, m.p. 155°–170° C.

Analysis: Calculated for $C_{16}H_{12}ClFNNaO_3$: C, 55.91; H, 3.52; N, 4.08 Found: C, 56.07; H, 3.63; N, 4.02.

EXAMPLE 64

2-Amino-3-(4-bromobenzoyl)-5-chloro-α-methylbenzene acetic acid, sodium salt

This compound was prepared by the procedure used to synthesize the compound of Example 63. The combination of 8.6 g (0.0236 mole) of 7-(4-bromobenzoyl)-5-chloro-1,3-dihydro-3-methyl-2H-indol-2-one and 180 ml of 3N sodium hydroxide gave 5.5 g (58%) of title compound, a yellow powder, m.p. 175°–180° C. (2-propanol).

Analysis: Calculated for $C_{16}H_{12}BrClNNaO_3$: C, 47.50; H, 2.99; N, 3.46 Found: C, 47.64; H, 3.34; N, 3.27.

EXAMPLE 65

2-Amino-3-(4-chlorobenzoyl)-α-ethylbenzeneacetic acid, sodium salt, hydrate [4:1]

This compound was prepared by the procedure used to synthesize the compound of Example 63. A combination of 8.0 g (0.027 mole) of 7-(4-chlorobenzoyl)-3-ethyl-1,3-dihydro-2H-indol-2-one and 180 ml of 3N sodium hydroxide gave, after successive recrystallizations, from 2-propanol and tetrahydrofuran, 4.1 g (45%) of title compound, a yellow powder, m.p. 140°–145° C.

Analysis: Calculated for $C_{17}H_{15}ClNNaO_3 \cdot 0.25H_2O$: C, 59.31; H, 4.54; N, 4.07 Found: C, 59.11; H, 4.44; N, 3.93.

EXAMPLE 66

2-Amino-3-(4-bromobenzoyl)-α-methylbenzeneacetic acid, sodium salt, hydrate, 2-propanol [4:1:2]

This compound was prepared by the procedure used to synthesize the compound of Example 63. A combination of 5.3 g (0.016 mole) of 7-(4-bromobenzoyl)-1,3-dihydro-3-methyl-2H-indol-2-one and 150 ml of 3N sodium hydroxide gave, after three recrystallizations from 2-propanol and one recrystallization from 2-propanol-methyl alcohol, 2.4 g (37%) of title compound, a yellow powder, m.p. 245°–247° C. with decomposition (loss of solvent at 110° C.).

Analysis: Calculated for $C_{16}H_{13}BrNNaO_3 \cdot 0.25H_2O \cdot 0.5C_3H_8O$: C, 51.93; H, 4.36; N, 3.46 Found: C, 51.92; H, 4.26; N, 3.50.

EXAMPLE 67

2-Amino-3-(2,4-dichlorobenzoyl)-α-methylbenzeneacetic acid, sodium salt, 2-propanol [1:1]

This compound was prepared by the procedure used to synthesize the compound of Example 63. A combination of 11.2 g (0.035 mole) of 7-(2,4-dichlorobenzoyl)-1,3-dihydro-3-methyl-2H-indol-2-one and 180 ml of 3N sodium hydroxide gave 8.5 g (58%) of title compound, yellow crystals, m.p. 125° C. (loss of solvent) (2-propanol).

Analysis: Calculated for $C_{16}H_{12}Cl_2NNaO_3 \cdot C_3H_8O$: C, 54.30; H, 4.76 N, 3.33 Found: C, 54.00; H, 4.66; N, 3.31.

EXAMPLE 68

2-Amino-3-(4-chlorobenzoyl)-5-chloro-α-methylbenzeneacetic acid, sodium salt

This compound was prepared by the procedure used to synthesize the compound of Example 63. A combination of 4.3 g (0.013 mole) of 7-(4-chlorobenzoyl)-5-chloro-1,3-dihydro-3-methyl-2H-indol-2-one and 120 ml of 3N sodium hydroxide gave 4.2 g of yellow solid, which was purified by dissolving in acetone, filtering, concentrating the filtrate, and triturating the residue with hot ligroin to give 4.1 g (85%) of title compound, a yellow powder, m.p. 155°–170° C. (with decomposition).

Analysis: Calculated for $C_{16}H_{12}Cl_2NNaO_3$: C, 53.36; H, 3.36; N, 3.89 Found: C, 53.55; H, 3.50; N, 3.82.

EXAMPLE 69

2-Amino-3-(4-bromobenzoyl)benzeneacetic acid, ethyl ester

A slurry of 35.6 g (0.1 mole) of 2-amino-3-(4-bromobenzoyl)benzeneacetic acid in 500 ml of dimethylformamide was treated with 32.0 g (0.2 mole) of ethyl iodide and stirred at ambient temperature for 24 hours. The mixture was filtered and the filtrate was poured into 3.5 liters of water. The solid which precipitated was collected by filtration, washed with water and recrystallized from absolute ethanol to give 26.8 g (74%) of title compound, gold needles, m.p. 107°–109° C.

Analysis: Calculated for $C_{17}H_{16}BrNO_3$: C, 56.37; H, 4.45; N, 3.87 Found: C, 56.22; H, 4.42; N, 3.87.

EXAMPLE 70

2-Amino-3-(4-bromobenzoyl)-5-fluoro-α-methylbenzeneacetic acid, sodium salt

This compound was prepared by the procedure used to synthesize the compound of Example 63. A combination of 12.5 g (0.036 mole) of 7-(4-bromobenzoyl)-5-fluoro-1,3-dihydro-3-methyl-2H-indol-2-one and 120 m 3N sodium hydroxide gave 5.3 g (38%) of title compound, yellow crytals, m.p. 162°–165° C. (98% aqueous ethanol).

Analysis: Calculated for $C_{16}H_{12}BrFNNaO_3$: C, 49.51; H, 3.12; N, 3.61 Found: C, 49,29; H, 3.14; N, 3.50.

EXAMPLE 71

2-Amino-3-benzoylbenzeneacetic acid, zinc salt

A solution of 6.36 g (0.021 mole) of 2-amino-3-benzoylbenzeneacetic acid, sodium salt in 100 ml of water was treated dropwise with a solution of 2.94 g of zinc sulfate heptahydrate (0.01 mole) in 100 ml of water. A precipitate instantly developed. The mixture was stirred for 10 minutes and the precipitate filtered off to give 4.4 g of product, recrystallized from toluene-petroleum ether, m.p. 95°–140° C.

Analysis: Calculated for $C_{30}H_{24}N_2O_6Zn$: C, 62.79; H, 4.22; N, 4.88 Found: C, 62.78; H, 4.17; N, 4.84.

EXAMPLE 72

2-Amino-3-benzoylbenzeneacetic acid, dihydroxyaluminum salt, monohydrate

A solution of 20.9 g (0.07 mole) of 2-amino-3-benzoylbenzeneacetic acid, sodium salt, monohydrate and 5.6 g (0.053 mole) of anhydrous sodium carbonate in 350 ml of deionized water stirred vigorously was treated dropwise with a solution of 8.5 g (0.035 mole) of aluminum trichloride hexahydrate in 85 ml of deionized water. After the addition was complete, the slurry was slowly heated to 70° C., gradually cooled to 50° C. and collected by filtration. The filter cake was washed with methyl alcohol and then stirred in 100 ml deionized water, heated to 50° C. and collected by filtration. The filter cake was washed with water and then methyl alcohol and dried at 56° C. to yield 9.0 g (78%) of title compound, a yellow powder, m.p. 193° C. (with decomposition).

Analysis: Calculated for $C_{15}H_{15}AlNO_4.H_2O$: C, 54.06; H, 4.84; N, 4.20 Found: C, 53.77; H, 4.46; N, 4.15.

EXAMPLE 73

2-Amino-3-benzoylbenzeneacetic acid, copper salt [2:1], monohydrate

A solution of 11.8 g (0.04 mole) of 2-amino-3-benzoylbenzeneacetic acid sodium salt monohydrate in 100 ml of water was filtered and the filtrate treated with a solution of 5.2 g (0.021 mole) of cupric sulfate pentahydrate in 25 ml of water. A green solid immediately precipitated. The mixture was stirred for an additional 5 min, and the solid was collected by filtration, washed with water and methyl alcohol, and dried to give 10.2 g (89%) of title compound, a yellow-green solid, m.p. 166° C. (with decomposition).

Analysis: Calculated for $C_{30}H_{26}N_2O_7Cu$: C, 61.06; H, 4.44; N, 4.75 Found: C, 60.95; H, 4.17; N, 4.75.

EXAMPLE 74

2-Amino-3-(4-bromobenzoyl)benzeneacetic acid, sodium salt, sesquihydrate

To a stirred mixture of 2.37 liters of toluene and 0.79 liters of ethyl alcohol was added 344 g (1.0 mole) of 7-(4-bromobenzoyl)-1,3-dihydro-2H-indol-2-one. A nitrogen purge was started and maintained during the following reaction. Sodium hydroxide 80 g (2.0 mole) as 50% aqueous solution was added in one portion. The deep red solution was heated to reflux and yellow solid began to precipitate. Refluxing was continued for an additional 1 hr and a sample was taken for TLC analysis [The TLC is run on silica gel plate using 5% ethyl acetate in benzene as eluant. The product remains at the origin and the 2-amino-3-(4-bromobenzoyl)benzeneacetic acid has an Rf of approximately 0.40]. The TLC plate showed only a trace of the starting oxindole was present. The mixture was cooled to 35° C. and 3.2 liters of diisopropyl ether was added. The mixture was chilled for 8–12 hr and the product was collected by filtration to give a 93% yield of crude product.

The dried solid was sized by passing it through a 40-mesh screen. The sized crude product was added to a mixture of 85% dimethoxyethane and 15% water at the rate of 1 g of crude per 6 ml of the solvent mixture. The entire mixture was then heated at reflux for 1 hr. The hot mixture was filtered to remove the undissolved solid. The filtrate was concentrated at reduced pressure to a damp sludge. The sludge was then slurried with 5 ml of diisopropyl ether per g of sludge. The solid was collected and dried to constant weight to give the title compound in 76% yield, m.p. 284°–286° C. (with decomposition).

Analysis: Calculated for $C_{15}H_{14}NO_{4.5}BrNa$: C, 47.02; H, 3.68; N, 3.66 Found: C, 47.74; H, 3.57; N, 3.66

EXAMPLE 75

2-Amino-3-(4-bromobenzoyl)-5-chlorobenzeneacetic acid, sodium salt, monohydrate

Utilizing the method of Example 74, 7-(4-bromobenzoyl)-5-chloro-1,3-dihydro-2H-indol-2-one was converted to the title compound, a yellow powder, m.p. 261°–63° C. (with decomposition).

Analysis: Calculated for $C_{15}H_{10}NO_3BrCl$: C, 44.09; H, 2.96; N, 3.43 Found: C, 43.85; H, 2.91; N, 3.36.

EXAMPLE 76

2-Amino-3-(4-bromobenzoyl)-5-chlorobenzeneacetic acid, ethyl ester

A solution of 40.9 g (0.1 mole) of 2-amino-3-(4-bromobenzoyl)-5-chlorobenzeneacetic acid, sodium salt, monohydrate in 400 ml of dimethylformamide was treated with 32.0 g (0.2 mole) of ethyl iodide and the solution was let stand at ambient temperature overnight. The solution was poured in 3.5 liters of cold water and a solid gradually crystallized. The solid was collected by filtration, washed with water, and recrystallized from absolute ethanol to yield 36.2 g (91%) of title compound, a yellow solid, m.p. 92°–94° C.

Analysis: Calculated for $C_{17}H_{15}BrClNO_3$: C, 51.48; H, 3.81; N, 3.53 Found: C, 51.34; H, 3.68; N, 3.55.

EXAMPLE 77

An oil-in-water cream such as, for example, is prepared in Formula A below (pH=Ca 7.0) containing 5 wt % of the active agent of Examples 21 and 74, namely, 2-amino-3-(4-bromobenzoyl)benzeneacetic acid as its sodium salt is administered in the amount of about 4 g of cream (200 mg active agent) to an area of approximately 15 $cm^2$ of skin of a human or animal suffering from pain and inflammation to obtain relief therefrom starting about 2–4 hr after administration and continuing for about 2–4 days, after which time more cream is applied to obtain further relief.

EXAMPLE 78

When in the procedure of Example 77, the compound of Example 1, namely, 2-amino-3- benzoylbenzeneacetic acid as its sodium salt is substituted as the active agent, pain and inflammation are controlled in the same manner.

EXAMPLE 79

When in the procedure of Example 77, the compound of Example 5, namely, 2-amino-3-benzylbenzeneacetic acid ethyl ester is substituted as the active agent, pain and inflammation are controlled.

EXAMPLE 80

When in the procedure of Example 77, the compound of Example 55, namely, 2-amino-3-(4-methylbenzoyl)-5-chlorobenzeneacetic acid as its sodium salt is substituted as the active agent, pain and inflammation are controlled.

EXAMPLE 81

When any compound in Examples 1–76 (other than those already used in Examples 77–80) is substituted in the procedure of Example 77 as the active agent, relief from pain and inflammation is also expectable.

EXAMPLE 82

A hydrogel preparation such as for example, in Formula C below, containing 5 wt % of the active agent of Examples 21 and 74, namely, 2-amino-3-(4-bromobenzyl)benzeneacetic acid as its sodium salt is administered in the amount of about 4 g of hydrogel (200 mg active agent) to an area of about 15 $cm^2$ of skin of a human or animal suffering from arthritic symptoms to obtain relief from pain and inflammation starting about 2–4 hr after administration and continuing for about 2–4 days after which time more of the hydrogel is applied to obtain further relief.

EXAMPLE 83

When in the procedure of Example 82, the compound of Example 1 namely 2-amino-3-benzoylacetic acid as its sodium salt is substituted as the active agent, pain and inflammation are controlled in the same manner.

EXAMPLE 84

When other compounds in the Examples 1–76 are substituted in the procedure of Example 83, relief from pain and inflammation is expectable.

EXAMPLE 85

An oil-in-water cream such as, for example, is prepared in Formula A below (pH=7,0) containing 5 wt % of the active agent of Examples 21 and 74, namely, 2-amino-3-(4-bromobenzoyl)benzeneacetic acid, as its sodium salt in the amount of about 4 g of cream (200 mg active agent) and contained in an occlusive device selected from those described below under "Pharmaceutical Compositions and Methods of Administration" is administered to a human or animal to provide relief from pain and inflammation when such symptoms exist.

EXAMPLE 86

When in the procedure of Example 85, the compound of Example 1, namely 2-amino-3-benzoylbenzeneacetic acid, as its sodium salt is substituted as the active agent, pain and inflammation are controlled in the same manner.

EXAMPLE 87

When any other compound in Examples 1–76 are substituted in the procedure of Example 85, relief from pain and inflammation is also expectable.

TABLE 1

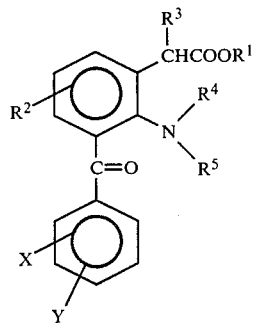

| Ex. No. | R¹ | R² | R³ | R⁴ | R⁵ | X | Y | M.P., °C | Literature Reference |
|---|---|---|---|---|---|---|---|---|---|
| 1 | —H | —H | —H | —H | —H | —H | —H | 122 | U.S. Pat. No. 4,126,635 Ex. 3 |
| 2 | —H (B) | 5-Cl | —H | —H | —H | —H | —H | 85–87 | U.S. Pat. No. 4,126,635 Ex. 6 |
| 3 | Na⁺ (E) | 5-OCH₃ | —H | —H | —H | —H | —H | 265* | U.S. Pat. No. 4,126,635 Ex. 7 |
| 4 | Na⁺ (G) | —H | —H | —H | —H | —H | —H | — | U.S. Pat. No. 4,126,635 Ex. 8 |
| 5 | —C₂H₅ | —H | —H | —H | —H | —H | —H | 77–78 | U.S. Pat. No. 4,126,635 Ex. 9 |
| 6 | Na⁺ (D) | —H | —H | —H | —H | 4-Cl | —H | 265* | U.S. Pat. No. 4,126,635 Ex. 14 |
| 7 | K⁺ (D) | —H | —H | —H | —H | —H | —H | — | U.S. Pat. No. 4,126,635 Ex. 16 |
| 8 | —C₂H₅ | —H | —H | —H | —H | 4-Cl | —H | 101–102 | U.S. Pat. No. 4,126,635 Ex. 21 |
| 9 | —H | —H | —H | —H | —H | 4-F | —H | 136–137 | U.S. Pat. No. 4,126,635 Ex. 22 |
| 10 | Na⁺ (D) | —H | —H | —H | —H | 4-F | —H | 240–250* | U.S. Pat. No. 4,126,635 Ex. 23 |
| 11 | —H | —H | —H | —H | —H | 4-OCH₃ | —H | 117–118 | U.S. Pat. No. 4,126,635 Ex. 24 |
| 12 | Mg⁺⁺ (H) | —H | —H | —H | —H | —H | —H | 150–190 | U.S. Pat. No. 4,126,635 Ex. 25 |
| 13 | Ca⁺⁺ (G) | —H | —H | —H | —H | —H | —H | 160–240* | U.S. Pat. No. 4,126,635 Ex. 26 |
| 14 | Na⁺ (D) | —H | —H | —H | —H | —H | —H | 254–255.5 | U.S. Pat. No. 4,126,635 Ex. 27 |
| 15 | Na⁺ (D) | 5-CH₃ | —H | —H | —H | 4-F | —H | 140–160 | GB 2,093,027 Ex. 1 |
| 16 | Na⁺ | 5-CH₃ | —H | —H | —H | 4-Cl | —H | 262 | GB 2,093,027 Ex. 2 |
| 17 | Na⁺ (D) | —H | —H | —H | —H | 4-SCH₃ | —H | 244–247 | U.S. Pat. No. 4,503,073 Ex. 4 |
| 18 | Na⁺ (C) | 5-Cl | —H | —H | —H | 4-SCH₃ | —H | 259–260 | U.S. Pat. No. 4,503,073 Ex. 10 |
| 19 | Na⁺ | 5-F | —H | —H | —H | 4-SCH₃ | —H | 241–244 | U.S. Pat. No. 4,503,073 Ex. 12 |
| 20 | Na⁺ (A) | 4-CH₃ | —H | —H | —H | —H | —H | 206–207 | Journal of Medicinal Chemistry (1984) 27, 1379–1388 Ex. 143 |
| 21 | Na⁺ | —H | —H | —H | —H | 4-Br | —H | 285* | Journal of Medicinal Chemistry (1984) 27, 1379–1388 Ex. 158 |
| 22 | Na⁺ (A) | 6-CH₃ | —H | —H | —H | —H | —H | 235–238 | Journal of Medicinal Chemistry (1984) 27, 1379–1388 Ex. 145 |
| 23 | Na⁺ (B) | 5-CH₃ | —H | —H | —H | —H | —H | 252* | Journal of Medicinal Chemistry (1984) 27, 1379–1388 Ex. 144 |
| 24 | Na⁺ (B) | —H | —H | —H | —H | 2-Cl | 4-Cl | 235–240* | Journal of Medicinal Chemistry (1984) 27, 1379–1388 Ex. 162 |
| 25 | Na⁺ (G) | 5-CH₃ | —H | —H | —H | 4-SCH₃ | —H | 225–260* | Journal of Medicinal Chemistry (1984) 27, 1379–1388 Ex. 168 |
| 26 | —H | 5-CH₃ | —H | —H | —H | 4-CH₃ | —H | 118–120* | Journal of Medicinal Chemistry (1984) 27, 1379–1388 Ex. 167 |
| 27 | Na⁺ (A) | 5-F | —H | —H | —H | 4-Cl | —H | 237–240 | Journal of Medicinal Chemistry (1984) 27, 1379–1388 Ex. 176 |
| 28 | Na⁺ (B) | 5-CH₃ | —H | —H | —H | 2-Cl | 4-Cl | 185–188 | Journal of Medicinal Chemistry (1984) 27, 1379–1388 Ex. 172 |
| 29 | Na⁺ | 5-Cl | —H | —H | —H | 4-Br | —H | 264–266* | Journal of Medicinal Chemistry (1984) 27, 1379–1388 Ex. 182 |
| 30 | Na⁺ (A) | 5-OCH₃ | —H | —H | —H | 4-Cl | —H | 215–220 | Journal of Medicinal Chemistry (1984) 27, 1379–1388 Ex. 165 |
| 31 | Na⁺ (B) | —H | —H | —H | —H | 2-Cl | 4-Br | 125–130 | Journal of Medicinal Chemistry (1984) 27, 1379–1388 Ex. 164 |
| 32 | Na⁺ (D) | 5-Cl | —H | —H | —H | 2-Cl | 4-Br | 235* | Journal of Medicinal Chemistry (1984) 27, 1379–1388 Ex. 185 |
| 33 | Na⁺ | 5-CH₃ | —H | —H | —H | 4-Br | —H | 267–270* | Journal of Medicinal Chemistry (1984) 27, 1379–1388 Ex. 171 |
| 34 | Na⁺ (B) | 5-Cl | —H | —H | —H | 4-I | —H | 275–278* | Journal of Medicinal Chemistry (1984) 27, 1379–1388 Ex. 183 |

TABLE 1-continued

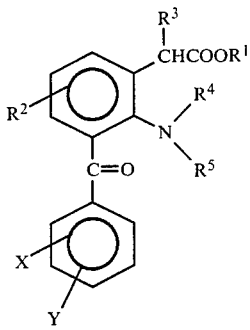

| Ex. No. | R¹ | R² | R³ | R⁴ | R⁵ | X | Y | M.P.,°C. | Literature Reference |
|---|---|---|---|---|---|---|---|---|---|
| 35 | Na⁺ (D) | 5-F | —H | —H | —H | 4-Br | —H | 244–247* | Journal of Medicinal Chemistry (1984) 27, 1379–1388 Ex. 177 |
| 36 | Na⁺ (B) | 5-Br | —H | —H | —H | 4-Br | —H | 268–269* | Journal of Medicinal Chemistry (1984) 27, 1379–1388 Ex. 187 |
| 37 | Na⁺ | 5-OCH₃ | —H | —H | —H | 4-Br | —H | 245–250* | Journal of Medicinal Chemistry (1984) 27, 1379–1388 Ex. 166 |
| 38 | Na⁺ (F) | —H | —H | —H | —H | 3-Cl | 4-Cl | 260–265* | Journal of Medicinal Chemistry (1984) 27, 1379–1388 Ex. 163 |
| 39 | Na⁺ | —H | —H | —H | —H | 4-F | —H | 260* | Journal of Medicinal Chemistry (1984) 27, 1379–1388 Ex. 154 |
| 40 | Na⁺ (B) | —H | —H | —H | —H | 4-OCH₃ | —H | 230–232* | Journal of Medicinal Chemistry (1984) 27 1379–1388 Ex. 149 |
| 41 | Na⁺ | 5-Cl | —H | —H | —H | —H | —H | 260* | Journal of Medicinal Chemistry (1984) 27 1379–1388 Ex. 148 |
| 42 | Na⁺ (D) | —H | —H | —H | —H | 2-Cl | —H | 260* | Journal of Medicinal Chemistry (1984) 27 1379–1388 Ex. 155 |
| 43 | Na⁺ (B) | —H | —H | —H | —H | 3-Cl | —H | 259–260* | Journal of Medicinal Chemistry (1984) 27 1379–1388 Ex. 156 |
| 44 | Na⁺ (B) | 5-F | —H | —H | —H | —H | —H | 253* | Journal of Medicinal Chemistry (1984) 27 1379–1388 Ex. 146 |
| 45 | Na⁺ | —H | —H | —H | —H | 4-CH₃ | —H | 264–264.5 | Journal of Medicinal Chemistry (1984) 27 1379–1388 Ex. 153 |
| 46 | Na⁺ (B) | —H | —H | —H | —H | 4-CF₃ | —H | 265* | Journal of Medicinal Chemistry (1984) 27 1379–1388 Ex. 151 |
| 47 | Na⁺ (A) | —H | —H | —H | —H | 2-CH₃ | —H | 268–272* | Journal of Medicinal Chemistry (1984) 27 1379–1388 Ex. 152 |
| 48 | Na⁺ (A) | 4-Cl | —H | —H | —H | —H | —H | 229–231 | Journal of Medicinal Chemistry (1984) 27 1379–1388 Ex. 147 |
| 49 | Na⁺ | 5-Cl | —H | —H | —H | 4-Cl | —H | >260* | Journal of Medicinal Chemistry (1984) 27 1379–1388 Ex. 181 |
| 50 | Na⁺ | 5-F | —H | —H | —H | 4-F | —H | 118–124 | Journal of Medicinal Chemistry (1984) 27 1379–1388 Ex. 175 |
| 51 | Na⁺ (A) | 5-F | —H | —H | —H | 4-CH₃ | —H | 239–244 | Journal of Medicinal Chemistry (1984) 27 1379–1388 Ex. 174 |
| 52 | Na⁺ (I) | 5-F | —H | —H | —H | 2-Cl | 4-Cl | 215–217 | Journal of Medicinal Chemistry (1984) 27 1379–1388 Ex. 178 |
| 53 | Na⁺ | —H | —H | —H | —H | 2-CH₃ | 4-CH₃ | 240* | Journal of Medicinal Chemistry (1984) 27 1379–1388 Ex. 161 |
| 54 | —H (C) | 5-Cl | —H | —H | —H | 4-OH | —H | 87–90 | Journal of Medicinal Chemistry (1984) 27 1379–1388 Ex. 184 |
| 55 | Na⁺ (C) | 5-Cl | —H | —H | —H | 4-CH₃ | —H | 259–260 | Journal of Medicinal Chemistry (1984) 27 1379–1388 Ex. 180 |
| 56 | Na⁺ (B) | 5-Br | —H | —H | —H | 4-Cl | —H | 270–275 | Journal of Medicinal |

TABLE 1-continued

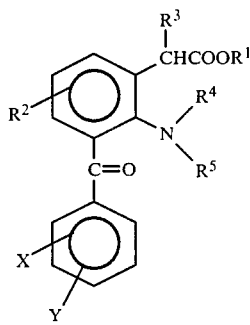

| Ex. No. | R¹ | R² | R³ | R⁴ | R⁵ | X | Y | M.P.,°C. | Literature Reference |
|---|---|---|---|---|---|---|---|---|---|
| 57 | Na⁺ (A) | —H | —H | —H | —H | 4-I | —H | 280–282 | Chemistry (1984) 27 1379–1388 Ex. 186 Journal of Medicinal Chemistry (1984) 27 1379–1388 Ex. 159 |
| 58 | —H | —H | —H | —CH₃ | —CH₃ | —H | —H | 144–146 | Journal of Medicinal Chemistry (1982), 25, 446–451 Ex. 26 |
| 59 | Na⁺ (G) | —H | —CH₃ | —H | —H | —H | —H | 95–103 | Journal of Medicinal Chemistry (1982), 25, 446–451 Ex. 15 |
| 60 | Zn⁺⁺ (B) | —H | —H | —H | —H | —H | —H | 144 | — |
| 61 | —C₂H₅ | 5-Cl | —H | —H | —H | —H | —H | 80–82 | — |
| 62 | Na⁺ (A) (I) | —H | —CH₃ | —H | —H | 4-Cl | —H | 130–140 | — |
| 63 | Na⁺ | 5-F | —CH₃ | —H | —H | 4-Cl | —H | 155–170 | — |
| 64 | Na⁺ | 5-Cl | —CH₃ | —H | —H | 4-Br | —H | 175–180 | — |
| 65 | Na⁺ (A) | —H | —CH₂CH₃ | —H | —H | 4-Cl | —H | 140–145 | — |
| 66 | Na⁺(A) (I) | —H | —CH₃ | —H | —H | 4-Br | —H | 245–247* | — |
| 67 | Na⁺ (J) | —H | —CH₃ | —H | —H | 2-Cl | 4-Cl | 125 | — |
| 68 | Na⁺ | 5-Cl | —CH₃ | —H | —H | 4-Cl | —H | 155–170* | — |
| 69 | —C₂H₅ | —H | —H | —H | —H | 4-Br | —H | 107–109 | — |
| 70 | Na⁺ | 5-F | —CH₃ | —H | —H | 4-Br | —H | 162–165 | — |
| 71 | Zn⁺⁺ | —H | —H | —H | —H | —H | —H | 95–140 | — |
| 72 | —Al (OH)₂ (D) | —H | —H | —H | —H | —H | —H | 193* | — |
| 73 | Cu⁺⁺ (D) | —H | —H | —H | —H | —H | —H | 166* | — |
| 74 | Na⁺ (E) | —H | —H | —H | —H | 4-Br | —H | 284–286* | — |
| 75 | Na⁺ (D) | 5-Cl | —H | —H | —H | 4-Br | —H | 261–263* | — |
| 76 | —C₂H₅ | 5-Cl | —H | —H | —H | 4-Br | —H | 92–94 | — |

Footnotes to Table I
* = with decomposition
(A) = 0.25 H₂O
(B) = 0.5 H₂O
(C) = 0.75 H₂O
(D) = .H₂O
(E) = 1.5 H₂O
(F) = 1.75 H₂O
(G) = 2 H₂O
(H) = 3 H₂O
(I) = .5 CH₃CH(OH)CH₃
(J) = .CH₃CH(OH)CH₃
R¹, R², R³, R⁴, R⁵, X and Y are as in Formula I.

KINETIC AND PHARMACOLOGICAL EVALUATION OF DERMAL APPLICATION

Cream Preparation - Formula A (Natural pH = 7.0).
See footnotes.

| Ingredient | Weight, grams |
|---|---|
| 1. Oil Phase Composition | |
| Methyl glucose sesquistearate[a] | 16.0 |
| Methyl gluceth -20 sesquistearate[b] | 24.0 |
| Methyl gluceth -20[c] | 40.0 |
| Acetylated lanolin[d] | 20.0 |
| Cetearyl alcohol[e] | 50.0 |
| Emulsifying wax, N.F.[f] | 50.0 |
| Heavy mineral oil[g] | 10.0 |
| White petrolatum U.S.P.[h] | 50.0 |
| Glyceryl monostearate[i] | 50.0 |
| Stearic acid, N.F.[j] | 25.0 |
| 2. Water Phase Composition | |
| 4-Hydroxybenzoic acid methyl ester*[k] | 1.8 |
| 4-Hydroxybenzoic acid propyl ester[l] | 0.2 |
| Magnesium aluminum silicate[m] | 15.0 |
| Deionized water | 648.0 |
| Total | 1000.0 |
| 3. Active agent | variable |

Mixing procedure:

Mix oil phase ingredients (1. above) and warm to 80° C. until the mixture melts. Separately, warm preservatives and water to 85° C. to dissolve and add and disperse the magnesium aluminum silicate to form the water phase (2. above). Add the water phase to stirred oil phase at 85° C. to obtain oil-in-water-based cream.

Evenly disperse active agent in desired proportion, usually up to 6 wt % in the cream.

Cream Preparation - Formula B (pH adjusted to 3.5). See footnotes.

| Ingredients | Weight, grams |
| --- | --- |
| 1. Oil Phase | |
| Same as Formula A | Same as Formula A (335.0 g) |
| 2. Water Phase | |
| Sodium benzoate** | 1.0 |
| Sodium propionate** | 1.0 |
| Deionized water | 632.0 |
| Magnesium aluminum silicate | 15.0 |
| HCl (as 1N solution to pH 3.5) | 16.0 |
| Total | 1000.0 |
| 3. Active agent | variable |

Footnotes to Formulas A and B:
[a]Amerchol glucate SS ® produced by Amerchol Corp., P. O. Box 351, Edison, N. J. 08817.
[b]Amerchol glucamate SSE-20 ®, Amerchol Corp.
[c]Amerchol glucam ® - Amerchol Corp.
[d]Amerchol modulan ® - Amerchol Corp.
[e]Crodacol CS-50 ® produced by Croda, Inc., 51 Madison Avenue, N. Y., N. Y. 10010.
[f]Palarwax ® - Croda, Inc.
[g]Kaydol ® produced by Witco Chem. Corp., Sonneborn Div., 277 Park Avenue, N. Y., N. Y. 10017.
[h]See the United States Pharmacopeia, 21st Ed. (1984).
[i]Cerasynt S.D. ® produced by Van Dyk & Co., Inc., Main and William Streets, Belleville, N. J. 07109.
[j]See The National Formulary, 16th Ed.
[k]Methyl paraben, N.F. See The National Formulary, 16th Ed.
[l]Propyl paraben. See The National Formulary, 16th Ed.
[m]Veegum K ® produced by R. T. Vanderbilt Co., Inc., 30 Winfield Street, Norwalk, Connecticut 06855
*4-Hydroxybenzoic acid esters are effective preservatives at pH = 7.
**Sodium benzoate and sodium propionate are effective as preservative under acid conditions.

Mixing procedure:
Same as for Formula A, except the hydrochloric acid is added to adjust to pH 3.5.

Hydrogel Preparation - Formula C.

| Ingredients | Weight, gram |
| --- | --- |
| Hydroxyethylcellulose, N.F.[a] | 20 |
| Water | 480 |
| Active agent of Formula I | variable |

Footnote to Formula C:
[a]Natrosol produced by Hercules, Inc., 910 Market Street, Wilmington, Del. 19899

Mixing procedure:
Warm the distilled water to about 80° C. Rapidly stir the water to create a vortex and add lump-free hydroxyethylcellulose to the vortex and continue stirring until a smooth viscous gel is obtained. The gel is poured into individual bottles which are then autoclaved at 121° C., 15 psig. for 15 minutes. Active ingredient is added prior to test use by levigation.

Preparation of Petrolatum Ointment—Formula D

Levigate known amount of active agent of Formula I in known amount of white petrolatum, U.S.P.

Kinetic Evaluation

Initial tests by an in vitro method with Formulas A, B, C and D above, using skin excised from hairless mice, involving diffusion tests by a method similar to that described by Holland, J. M. et al. in TOXICOLOGY AND APPLIED PHARMACOLOGY 72: 272-280 (1984), gave transdermal flux with 1% wt % concentrations of the compound of Example 74 in the following order: Formula A (pH=7.0)>Formula B (pH=3.5)>Formula C (hydrogel)>Formula D (petrolatum). In addition, Formula A gave the most reproducible flux.

In the kinetic evaluation method the formulations A, B, C and D were applied in separate tests to the epidermal side of the excised mouse skin mounted on a perfusion cell while a culture medium [Hank's Balanced Salts solution with 50 mM HEPES buffer, pH=7.40 (Flow Laboratories, Dublin, Va.) gassed with 95% $O_2$/5% $CO_2$ at 37° C. and protected with antibiotics] was pumped through the perfusion chamber against the dermal side of the skin at 2 ml/hr. Perfusate samples were collected for 18 hr. The net $\mu g$ of compound (Ex. 74) transferred to the perfusate was plotted versus time to give a sigmoidal curve. The linear portion of the curve was determined by inspection and the slope and intercepts of this line segment was calculated by linear regression analysis. From this and the known area of skin, the flux of the drug was calculated and results given in Table 2.

TABLE 2

Transdermal Flux of Compound of Example 74 using Hairless Mouse Skin

| Formulation | Flux, $\mu g/hr/cm^{2}$[a] |
| --- | --- |
| Formula A (pH = 7.0) | 0.52 ± 0.01 |
| Formula B (pH = 3.5) | 0.37 ± 0.20 |
| Formula C (Hydrogel) | 0.18 ± 0.02 |
| Formula D (Petrolatum) | 0.07 ± 0.02 |

[a]Linear period of permeation.
Mean ± standard deviation, n = 2

Antiinflammatory Test Procedure—Carrageenan Induced Rat-Paw Edema

On the day prior to the test, an area of about 1"×1" of the lower back just above the tail of each of the rats was shaved and depilated with the commercially available hair removal preparation—Nair ®. The rats were returned to the vivarium for feed and water.

The following day each rat was weighed and the volume of the left hind limb recorded. The rats were randomized into groups. Creams were applied in the following manner: 0.2 ml of the cream vehicle (control—no active agent) or formulation containing active ingredient was rubbed thoroughly onto the shaved depilated area of the rat's back for 10-15 seconds. The rats were immediately placed into plexiglass observation cylinders to restrict movement so as to prohibit accidental oral ingestion of the cream. The rats were then placed in a quiet room for 4 hr. Four hours after dosing, 0.1 ml of 1% carrageenan was injected into the left hind limb of each rat. The rats were returned to their observation cylinders and placed in the quiet room for an additional 3 hr time, after which the volume of the left hind limb was determined. The degree of edema was determined by subtracting limb volume at 0 time from the volume determined 3 hr after carrageenan injection. Two tail Dunnett's t-tests were used to compare the edema of the treated groups with the appropriate controls (Dunnet, C. W. (1955); J. AM. STAT. ASSOC. 50: 1096-1121).

Antiinflammatory Test Results—Dermal Application

Several compounds of Formula I were mixed with the creams as prepared above so as to obtain cream containing 3.2 weight percent of each compound based on the weight of free acid or the ester. Rats in groups of 6 (randomized) were each treated with 0.2 ml of the cream containing the compound using the foregoing Carrageenan Induced Rat-Paw Edema test. The control rats were treated with cream having no test compound. Results are in Table 3.

TABLE 3

Carrageenan-Induced Rat-Paw Edema Study - Various Compounds in Transdermal Administration

| Test Compound (Example No.) | Cream Formula[a] | Measurement of Edema at 3 hr. (ml ± S.D.) | % Change | Significance |
|---|---|---|---|---|
| Control | B, pH = 3.5 | 0.98 ± 0.18 | — | |
| 74[b][c] | B, pH = 3.5 | 0.38 ± 0.18 | −61 | p = <0.05 |
| Control | B, pH = 3.5 | 0.86 ± 0.30 | — | |
| 74[b][c] | B, pH = 3.5 | 0.48 ± 0.17 | −44 | p = <0.05 |
| Control | A, pH = 7.0 | 0.82 ± 0.13 | — | |
| 75[b][c] | A, pH = 7.0 | 0.47 ± 0.21 | −43 | p = <0.05 |
| Control | A, pH = 7.0 | 0.80 ± 0.28 | — | |
| 75[b][c] | A, pH = 7.0 | 0.20 ± 0.15 | −75 | p = <0.05 |
| Control | A, pH 7.0 | 0.93 ± 0.32 | — | |
| 5[b] | A, pH = 7.0 | 0.27 ± 0.18 | −71 | p = <0.05 |
| 19[b][c] | A, pH = 7.0 | 0.55 ± 0.14 | −41 | p = <0.05 |
| 55[b][c] | A, pH = 7.0 | 0.33 ± 0.20 | −64 | p = <0.05 |
| 57[b][c] | A, pH = 7.0 | 0.40 ± 0.14 | −57 | p = <0.05 |
| 69[b] | A, pH = 7.0 | 0.50 ± 0.20 | −46 | p = <0.05 |

[a] 0.2 ml of cream.
[b] Cream contains 3.2% by weight of compound.
[c] Calculated on the basis of free acid.

In addition, one preferred compound was tested further using the foregoing Carrageenan-Induced Rat-Paw Edema test at various concentrations in the cream of Formula B (pH=3.5). Results are in Table 4.

TABLE 4

Carrageenan-Induced Rat-Paw Edema Study - Varied Concentration of 2-Amino-3-(4-bromobenzoyl)benzeneacetic acid, sodium salt hydrate Transdermal Application

| Test Compound | Concentration of Test Compound in Cream % (W/W)[a] | Dose, mg/kg | 3 Hr. Edema, ml ± S.D. | % Change |
|---|---|---|---|---|
| Control | — | — | 0.98 ± 0.18 | — |
| Ex. 74 | 3.16 | 36.5 | 0.38 ± 0.18[b] | −61 |
| " | 1.0 | 11.9 | 0.42 ± 0.10[b] | −57 |
| " | 0.32 | 3.7 | 0.37 ± 0.19[b] | −62 |
| " | 0.10 | 1.1 | 0.42 ± 0.21[b] | −57 |
| " | 0.032 | 0.37 | 0.73 ± 0.33 | −26 |
| Control | — | — | 0.86 ± 0.34 | — |
| Ex. 74 | 3.16 | 31.5 | 0.48 ± 0.17[b] | −44 |
| " | 1.0 | 10.3 | 0.37 ± 0.05[b] | −57 |
| " | 0.32 | 3.0 | 0.42 ± 0.15[b] | −52 |
| " | 0.10 | 0.94 | 0.55 ± 0.20 | −36 |
| " | 0.032 | 0.32 | 1.05 ± 0.22 | +22 |
| " | 0.01 | 0.10 | 0.88 ± 0.33 | +3 |

[a] Calculated on the basis of the free acid.
[b] Significantly different from the control; p < 0.05, Dunnetts' t-test.

In another comparative study, using the Carrageenan-Induced Rat-Paw-Edema test, the compound of Example 74 in Formula B cream, above (pH=3.5) was found to be about as active applied dermally as it was orally for a given dose, whereas indomethacin was found to be markedly less active when applied dermally than when given orally for a given dose. The compound of Example 74, applied dermally to rats, was more active against the Edema than indomethacin applied dermally or orally.

ANALGETIC TESTS IN DERMAL APPLICATION TO MICE

Cream Preparation

Active agent was incorporated into the cream described under Formual A above (pH=7.0) at various concentrations calculated on a free acid basis.

Analgetic Test Procedure—Acetylcholine Induced Abdominal Constriction Test in Mice Mice were prepared for the test by shaving an area measuring $\frac{3}{4}'' \times \frac{3}{4}''$ on their backs behind their heads and then depilating with Nair ®, a cosmetic hair remover. The mice were given free access to feed and water prior to the experiment. On the following day the mice were weighed and fitted with a cardboard collar ($1\frac{3}{4}'' \times 1\frac{3}{4}''$ with a $\frac{1}{2}''$ hole in the center) around the neck to prevent ingestion of applied compounds. The mice were randomized into groups of 10 using random tables generated by the IBM scrambler. A table of random permutations of blocks of order 3 was used to select the control and treated groups. The randomized mice were fed and placed in individual observation cages 1 hr prior to application of 50 microliters of the cream (by rubbing onto the skin for approximately 10 seconds).

The mice acting as controls were treated with cream having no test compound in it. Four hours after the application of the cream to the depilated area, acetylcholine bromide was injected intraperitoneally at 6 mg/kg (10 ml/kg in saline) with a plastic syringe with a 5/8 inch, 25-gauge disposable needle. Each mouse was immediately placed under an inverted 1 liter beaker and observed for 3 minutes for the presence of abdominal constriction. If no abdominal constriction was observed during this period, the response was considered blocked. $ED_{50}$ and 95% confidence limits were determined by computer using a probit analysis method. Ten mice were used at each concentration, including controls.

The following results in Table 5 were obtained using the foregoing method using the cream of Formula A (pH=7.0) as described above having mixed therein the compound of Example 74 in comparison to controls wherein no test compound was present.

TABLE 5

Dose Relationship of Dermally Applied Cream Containing 2-Amino-3-(4-bromobenzoyl)benzeneacetic acid sodium salt hydrate to Analgetic Effect[a]

| Compound Used in pH = 7.0 Cream (Formula A) Vehicle | Concentration of Agent in 50 µl Cream wt. % | % Block | $ED_{50}$ as % Concentration of Agent in Cream (95% Confidence Limits) |
|---|---|---|---|
| Control (Cream only) | 0 | 0 | |
| Ex. 74 | 0.01 | 0 | |
| | 0.032 | 20 | 0.128 |
| | 0.10 | 60 | |
| | 0.32 | 80 | (0.06–0.29) |
| | 1.0 | 80 | |
| | 3.16 | 90 | |

[a] 4 Hr pretreatment time with cream prior to challenge with acetylcholine bromide.

PHARMACEUTICAL COMPOSITIONS AND METHODS OF ADMINISTRATION

Pharmaceutical compositions for transdermal administration to animals and humans are comprised of at least one of the compounds of Formula I as active agent and a carrier which is not unduly destabilizing to the active agent and which is non-toxic to the skin and allows delivery of the agent for systemic absorption into the blood stream via the skin. The carrier may take any number of different forms such as creams and ointments, pastes, gels and occlusive devices.

As stated above, the carrier should not be unduly destabilizing to the active agent. Inasmuch as the 2-amino-3-benzoylbenzeneacetic acids and esters thereof tend to degrade to benzoyl-indolin-2-ones under acidic conditions, low pH of the carrier+active agent should be avoided. Considering also that high pH above about 8 is irritating to the skin, the pH of the pharmaceutical composition is ideally between about 6.5 and about 8.0. Therefore, a pH of about 6.5 to about 8.0 is preferred. Most preferably the pH of the carrier plus active agent is about 7.0.

The creams and ointments may be viscous liquid at semisolid emulsions of either the oil-in-water or water-in-oil type, preferably the oil-in-water type.

Pastes comprised of absorptive powders dispersed in petroleum or hydrophilic petroleum containing the active agent may be used.

Various gels known in the art and illustrated by Formula C above are suitable carriers.

A variety of types of occlusive devices (plasters) may be used to release active agents of Formula I to the skin of animals and humans. One type of device may be comprised of an impermeable outer backing covering the top and sides of a reservoir containing the active agent in the form of creams, ointments, and the like, a semipermeable membrane (release control membrane) across the bottom of the reservoir and a contact adhesive on the edges of the sides around the reservoir formed by the outer backing and an impermeable peel strip over the semipermeable membrane and against the adhesive edges. Such an occlusive device is illustrated in PHYSICIANS' DESK REFERENCE, 39th Ed. (1985), pages 873–874. Silicone membrane may be suitably employed as the semipermeable membrane.

Another type of suitable occlusive device may have a reservoir comprised of a firmer matrix containing the active agent of Formula I, which act as a reservoir and eliminates the need for a semipermeable membrane, i.e., the matrix acts as a reservoir and a release controlling system combined. The device will have an impermeable membrane over the top and sides and a contact adhesive on the edges of the sides around the reservoir. One such matrix is provided by a mixture of glycerine, water, lactose, polyvinyl alcohol, polyvinyl pyrrolidinone and preservatives comparable for one system used for delivery of nitroglycerine. See PHYSICIANS' DESK REFERENCE, 39th Ed. (1985), page 1050.

Still another type of occlusive device may be comprised of an impermeable outer backing over an adhesive which contains the active ingredient of Formula I and an impermeable peal strip over the adhesive. In this type the drug is dispensed from the adhesive.

The occlusive devices may be attached to the skin in any outer part of the body, preferably so as not to interfere with movement of appendages. Likewise, creams and ointments may be applied to the skin in any part of the body.

Any of the carriers may contain penetration enhancers, i.e., materials that have a direct effect on the permeability of the skin. The preferred creams Formulas A and B contain a large amount of water which is one type of penetration enhancer. Other suitable penetration enhancers are eugenol, dimethylformamide, dimethylsulfoxide, dimethylacetamide, N,N-diethyl-m-toluamide (DEET) and 1-dodecylazacycloheptan-2-one (Azone Advantageously, the compositions are formulated or dispensed as dosage units, each unit being adapted to supply a fixed dose of active ingredients. Unit doses of creams or ointments may be supplied in small packets, e.g., sealed foil packets, which may be torn open on an end and material in carrier squeezed out or measured from a tube. The occlusive devices as described above automatically become unit dosages. It is only necessary that the active ingredient constitute an effective amount, i.e., such that a suitable effective dosage will be consistent with the dosage form employed. The exace individual dosages, as well as daily dosages, will of course be determined according to standard medical principles under the direction of a physician or veterinarian.

Based on limited tests with animals, for example, Formula A above, application of a cream (pH 6.5–8.0) containing 3 to 6 wt % active agent (Formula I) in the amount so as to contain a total of 50–300 mg for an adult human and spread over 5–15 cm² area of skin will be sufficient to relieve pain and inflammation starting at 4 hr after administration and up to 72 hr. Administration contemplated is once every 2–4 days. Delivery of similar amounts by other vehicles and occlusion devices as unit dosages is contemplated. However, the scope of the invention is not to be limited by these contemplations due to uncertainty in transposing from animal data.

What is claimed is:

1. A method of treating animals or humans to alleviate pain or inflammation by applying to the skin of said animals or humans a transdermal preparation comprised of a pharmaceutical carrier containing therein a pain or inflammation alleviating amount of compound of the formula:

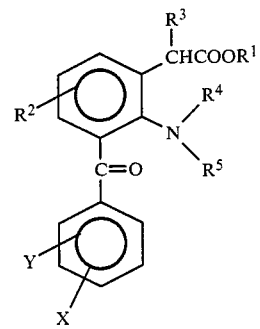

wherein;
$R^1$ is hydrogen, loweralkyl or a pharmaceutically acceptable cation;
$R^2$ is hydrogen, halogen, loweralkyl or loweralkoxy;
$R^3$, $R^4$ and $R^5$ are hydrogen or loweralkyl;
X is hydrogen, halogen, loweralkyl, hydroxy, loweralkoxy, nitro, trifluoromethyl or S-loweralkyl; and Y is hydrogen, loweralkyl, loweralkoxy, nitro or trifluoromethyl; and the hydrates thereof.

2. The method of claim 1 wherein the transdermal preparation is a cream and the pH of said cream is 6.5–8.0.

3. The method of claim 1 wherein the transdermal preparation is contained in an occlusive device.

4. The method of claim 1 wherein $R^1$ is sodium ion.

5. The method of claim 1 wherein the compound is 2-amino-3-benzoylacetic acid or a pharmaceutically acceptable salt thereof.

6. The method of claim 1 wherein the compound is 2-amino-3-benzoyl-5-chlorobenzeneacetic acid or a pharmaceutically acceptable salt thereof.

7. The method of claim 1 wherein the compound is 2-amino-3-benzoyl-5-methoxybenzeneacetic acid or a pharmaceutically acceptable salt thereof.

8. The method of claim 1 wherein the compound is 2-amino-3-benzoylbenzeneacetic acid, sodium salt, dihydrate.

9. The method of claim 1 wherein the compound is 2-amino-3-benzoylbenzeneacetic acid, ethyl ester.

10. The method of claim 1 wherein the compound is 2-amino-3-(4-chlorobenzoyl)benzeneacetic acid or a pharmaceutically acceptable salt thereof.

11. The method of claim 1 wherein the compound is 2-amino-3-benzoylbenzeneacetic acid, potassium salt, monohydrate.

12. The method of claim 1 wherein the compound is 2-amino-3-(4-chlorobenzoyl)benzeneacetic acid, ethyl ester.

13. The method of claim 1 wherein the compound is 2-amino-3-(4-fluorobenzoyl)benzeneacetic acid or a pharmaceutically acceptable salt thereof.

14. The method of claim 1 wherein the compound is 2-amino-3-(4-fluorobenzoyl)benzeneacetic acid, sodium salt, monohydrate.

15. The method of claim 1 wherein the compound is 2-amino-3-(4-methoxybenzoyl)benzeneacetic acid or a pharmaceutically acceptable salt thereof.

16. The method of claim 1 wherein the compound is 2-amino-3-benzoylbenzeneacetic acid, megnesium salt, trihydrate.

17. The method of claim 1 wherein the compound is 2-amino-3-benzoylbenzeneacetic acid, calcium salt, dihydrate.

18. The method of claim 1 wherein the compound is 2-amino-3-benzoylbenzeneacetic acid sodium salt, monohydrate.

19. The method of claim 1 wherein the compound is 2-amino-3-(4-fluorobenzoyl)-5-methylbenzeneacetic acid, sodium salt, monohydrate.

20. The method of claim 1 wherein the compound is 2-amino-3-(4-chlorobenzoyl)-5-methylbenzeneacetic acid or a pharmaceutically acceptable salt thereof.

21. The method of claim 1 wherein the compound is 2-amino-3-[(4-methylthio)benzoyl]benzene acetic acid or a pharmaceutically acceptable salt thereof.

22. The method of claim 1 wherein the compound is 2-amino-3-[(4-methylthio)benzoyl]-5-chlorobenzeneacetic acid or a pharmaceutically acceptable salt thereof.

23. The method of claim 1 wherein the compound is 2-amino-3-[(4-methylthio)benzoyl]-5-fluorobenzeneacetic acid or a pharmaceutically acceptable salt thereof.

24. The method of claim 1 wherein the compound is 2-amino-3-benzoyl-4-methylbenzeneacetic acid or a pharmaceutically acceptable salt thereof.

25. The method of claim 1 wherein the compound is 2-amino-3-(4-bromobenzoyl)benzeneacetic acid or a pharmaceutically acceptable salt thereof.

26. The method of claim 1 wherein the compound is 2-amino-3-benzoyl-6-methylbenzeneacetic acid or a pharmaceutically acceptable salt thereof.

27. The method of claim 1 wherein the compound is 2-amino-3-benzoyl-5-methylbenzeneacetic acid or a pharmaceutically acceptable salt thereof.

28. The method of claim 1 wherein the compound is 2-amino-3-(2,4-dichlorobenzoyl)benzeneacetic acid or a pharmaceutically acceptable salt thereof.

29. The method of claim 1 wherein the compound is 2-amino-3-[4-(methylthio)benzoyl]-5-methylbenzeneacetic acid or a pharmaceutically acceptable salt thereof.

30. The method of claim 1 wherein the compound is 2-amino-3-(4-methylbenzoyl)-5-methylbenzeneacetic acid or a pharmaceutically acceptable salt thereof.

31. The method of claim 1 wherein the compound is 2-amino-3-(4-chlorobenzoyl)-5-fluorobenzeneacetic acid or a pharmaceutically acceptable salt thereof.

32. The method of claim 1 wherein the compound is 2-amino-3-(2,4-dichlorobenzoyl)-5-methylbenzeneacetic acid or a pharmaceutically acceptable salt thereof.

33. The method of claim 1 wherein the compound is 2-amino-3-(4-bromobenzoyl)-5-chlorobenzeneacetic acid or a pharmaceutically acceptable salt thereof.

34. The method of claim 1 wherein the compound is 2-amino-3-(4-chlorobenzoyl)-5-methoxybenzeneacetic acid or a pharmaceutically acceptable salt thereof.

35. The method of claim 1 wherein the compound is 2-amino-3-(4-bromo-2-chlorobenzoyl)benzeneacetic acid or a pharmaceutically acceptable salt thereof.

36. The method of claim 1 wherein the compound is 2-amino-3-(4-bromo-2-chlorobenzoyl)-5-chlorobenzeneacetic acid or a pharmaceutically acceptable salt thereof.

37. The method of claim 1 wherein the compound is 2-amino-3-(4-bromobenzoyl)-5-methylbenzeneacetic acid or a pharmaceutically acceptable salt thereof.

38. The method of claim 1 wherein the compound is 2-amino-3-(4-iodobenzoyl)-5-chlorobenzeneacetic acid or a pharmaceutically acceptable salt thereof.

39. The method of claim 1 wherein the compound is 2-amino-3-(4-bromobenzoyl)-5-fluorobenzeneacetic acid or a pharmaceutically acceptable salt thereof.

40. The method of claim 1 wherein the compound is 2-amino-3-(4-bromobenzoyl)-5-bromobenzeneacetic acid or a pharmaceutically acceptable salt thereof.

41. The method of claim 1 wherein the compound is 2-amino-3-(4-bromobenzoyl)-5-methoxybenzeneacetic acid or a pharmaceutically acceptable salt thereof.

42. The method of claim 1 wherein the compound is 2-amino-3-(3,4-dichlorobenzoyl)benzeneacetic acid or a pharmaceutically acceptable salt thereof.

43. The method of claim 1 wherein the compound is 2-amino-3-(4-fluorobenzoyl)benzeneacetic acid, sodium salt.

44. The method of claim 1 wherein the compound is 2-amino-3-(4-methoxybenzoyl)benzeneacetic acid, sodium salt, hemihydrate.

45. The method of claim 1 wherein the compound is 2-amino-3-benzoyl-5-chlorobenzeneacetic acid, sodium salt.

46. The method of claim 1 wherein the compound is 2-amino-3-(2-chlorobenzoyl)benzeneacetic acid or a pharmaceutically acceptable salt thereof.

47. The method of claim 1 wherein the compound is 2-amino-3-(3-chlorobenzoyl)benzeneacetic acid or a pharmaceutically acceptable salt thereof.

48. The method of claim 1 wherein the compound is 2-amino-3-benzoyl-5-fluorobenzeneacetic acid or a pharmaceutically acceptable salt thereof.

49. The method of claim 1 wherein the compound is 2-amino-3-(4-methylbenzoyl)benzeneacetic acid or a pharmaceutically acceptable salt thereof.

50. The method of claim 1 wherein the compound is 2-amino-3-[4-(trifluoromethyl)benzoyl]benzeneacetic acid or a pharmaceutically acceptable salt thereof.

51. The method of claim 1 wherein the compound is 2-amino-3-(2-methylbenzoyl)benzeneacetic acid or a pharmaceutically acceptable salt thereof.

52. The method of claim 1 wherein the compound is 2-amino-3-benzoyl-4-chlorobenzeneacetic acid or a pharmaceutically acceptable salt thereof.

53. The method of claim 1 wherein the compound is 2-amino-3-(4-chlorobenzoyl)-5-chlorobenzeneacetic acid or a pharmaceutically acceptable salt thereof.

54. The method of claim 1 wherein the compound is 2-amino-3-(4-fluorobenzoyl)-5-fluorobenzeneacetic acid or a pharmaceutically acceptable salt thereof.

55. The method of claim 1 wherein the compound is 2-amino-3-(4-methylbenzoyl)-5-fluorobenzeneacetic acid or a pharmaceutically acceptable salt thereof.

56. The method of claim 1 wherein the compound is 2-amino-3-(2,4-dichlorobenzoyl)-5-fluorobenzeneacetic acid or a pharmaceutically acceptable salt thereof.

57. The method of claim 1 wherein the compound is 2-amino-3-(2,4-dimethylbenzoyl)benzeneacetic acid or a pharmaceutically acceptable salt thereof.

58. The method of claim 1 wherein the compound is 2-amino-3-(4-hydroxybenzoyl)-5-chlorobenzeneacetic acid or a pharmaceutically acceptable salt thereof.

59. The method of claim 1 wherein the compound is 2-amino-3-(4-methylbenzoyl)-5-chlorobenzeneacetic acid or a pharmaceutically acceptable salt thereof.

60. The method of claim 1 wherein the compound is 2-amino-3-(4-chlorobenzoyl)-5-bromobenzeneacetic acid or a pharmaceutically acceptable salt thereof.

61. The method of claim 1 wherein the compound is 2-amino-3-(4-iodobenzoyl)benzeneacetic acid or a pharmaceutically acceptable salt thereof.

62. The method of claim 1 wherein the compound is 2-dimethylamino-3-benzoylbenzeneacetic acid or a pharmaceutically acceptable salt thereof.

63. The method of claim 1 wherein the compound is 2-amino-3-benzoyl-α-methylbenzeneacetic acid or a pharmaceutically acceptable salt thereof.

64. The method of claim 1 wherein the compound is 2-amino-3-benzoyl-α-methylbenzeneacetic acid, zinc salt, hemihydrate.

65. The method of claim 1 wherein the compound is 2-amino-3-benzoyl-5-chlorobenzeneacetic acid, ethyl ester.

66. The method of claim 1 wherein the compound is 2-amino-3-(4-chlorobenzoyl)-α-methylbenzeneacetic acid or a pharmaceutically acceptable salt thereof.

67. The method of claim 1 wherein the compound is 2-amino-3-(4-chlorobenzoyl)-5-fluoro-α-methylbenzeneacetic acid or a pharmaceutically acceptable salt thereof.

68. The method of claim 1 wherein the compound is 2-amino-3-(4-bromobenzoyl)-5-chloro-α-methylbenzeneacetic acid or a pharmaceutically acceptable salt thereof.

69. The method of claim 1 wherein the compound is 2-amino-3-(4-chlorobenzoyl)-α-ethylbenzeneacetic acid or a pharmaceutically acceptable salt thereof.

70. The method of claim 1 wherein the compound is 2-amino-3-(4-bromobenzoyl)-α-methylbenzeneacetic acid or a pharmaceutically acceptable salt thereof.

71. The method of claim 1 wherein the compound is 2-amino-3-(2,4-dichlorobenzoyl)-α-methylbenzeneacetic acid or a pharmaceutically acceptable salt thereof.

72. The method of claim 1 wherein the compound is 2-amino-3-(4-chlorobenzoyl)-5-chloro-α-methylbenzeneacetic acid or a pharmaceutically acceptable salt thereof.

73. The method of claim 1 wherein the compound is 2-amino-3-(4-bromobenzoyl)benzeneacetic acid, ethyl ester.

74. The method of claim 1 wherein the compound is 2-amino-3-(4-bromobenzoyl)-5-fluoro-α-methylbenzeneacetic acid or a pharmaceutically acceptable salt thereof.

75. The method of claim 1 wherein the compound is 2-amino-3-benzoylbenzeneacetic acid, zinc salt.

76. The method of claim 1 wherein the compound is 2-amino-3-benzoylbenzeneacetic acid, dihydroxyaluminum salt, monohydrate.

77. The method of claim 1 wherein the compound is 2-amino-3-benzoylbenzeneacetic acid copper salt, monohydrate.

78. The method of claim 1 wherein the compound is 2-amino-3-(4-bromobenzoyl)benzeneacetic acid, sodium salt, sesquihydrate.

79. The method of claim 1 wherein the compound is 2-amino-3-(4-bromobenzoyl)-5-chlorobenzeneacetic acid, sodium salt, monohydrate.

80. The method of claim 1 wherein the compound is 2-amino-3-(4-bromobenzoyl)-5-chlorobenzeneacetic acid, ethyl ester.

* * * * *